(12) United States Patent
Tang et al.

(10) Patent No.: US 7,191,639 B2
(45) Date of Patent: Mar. 20, 2007

(54) ON-CHIP MAGNETIC FORCE ACTUATION OF MICROCANTILEVERS BY COPLANAR COILS

(75) Inventors: Hongxing Tang, Pasadena, CA (US); Michael L. Roukes, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 186 days.

(21) Appl. No.: 10/815,517

(22) Filed: Apr. 1, 2004

(65) Prior Publication Data

US 2004/0244488 A1 Dec. 9, 2004

Related U.S. Application Data

(60) Provisional application No. 60/461,257, filed on Apr. 8, 2003.

(51) Int. Cl.
*G01N 29/02* (2006.01)
(52) U.S. Cl. .................. 73/24.06; 73/54.41; 73/61.49; 73/61.79; 73/64.53
(58) Field of Classification Search .................. None
See application file for complete search history.

(56) References Cited

U.S. PATENT DOCUMENTS 3,638,488 A * 2/1972 Meijer ...................... 73/861.18

| | | | | |
|---|---|---|---|---|
| 5,513,518 A | * | 5/1996 | Lindsay | ........................ 73/105 |
| 2002/0092340 A1 | * | 7/2002 | Prater et al. | ................ 73/24.02 |
| 2002/0092359 A1 | * | 7/2002 | Lange et al. | ................... 73/779 |
| 2002/0166962 A1 | * | 11/2002 | Roukes et al. | .............. 250/306 |
| 2002/0178831 A1 | * | 12/2002 | Takada | ......................... 73/779 |
| 2005/0276726 A1 | * | 12/2005 | McGill et al. | ................. 422/96 |

OTHER PUBLICATIONS

Bargatin et al., "Sensitive detection of nanomechanical motion using peizoresistive signal downmixing." Applied Physics Letters, 86, 133109-1-133109-3, 2005.
Judy et al., "Magnetic Microactuation of Polysilicon Flexure Structures," IEEE Journal of Microelectromechanical Systems, vol. 4, No. 4, Dec. 1995, pp. 162-169.
Yi et al., "Magnetic Actuation of Hinged Microstructures," IEEE Journal of Microelectromechanical Systems, vol. 8, No. 1, Mar. 1999, pp. 10-17.

* cited by examiner

*Primary Examiner*—Hezron Williams
*Assistant Examiner*—Rose M. Miller
(74) *Attorney, Agent, or Firm*—Foley & Lardner LLP

(57) ABSTRACT

An on-chip coil is provided in a micromachined device for magnetic actuation of a nanoelectromechanical microcantilever. The novel geometry involves a three dimensional solenoid or planar coil carrying high current that generates a large enough magnetic field in its close proximity to a permalloy thin film patch or columnar magnet disposed on the distal end of the piezoresistive microcantilever to effectively interacts with the magnetic thin film deposited on the microcantilever. The device comprises an effective actuators which can be integrated with biofunctionalized cantilever arrays in hybrid semiconductor-microfluidics devices for the analysis and detection of biological analytes.

43 Claims, 10 Drawing Sheets

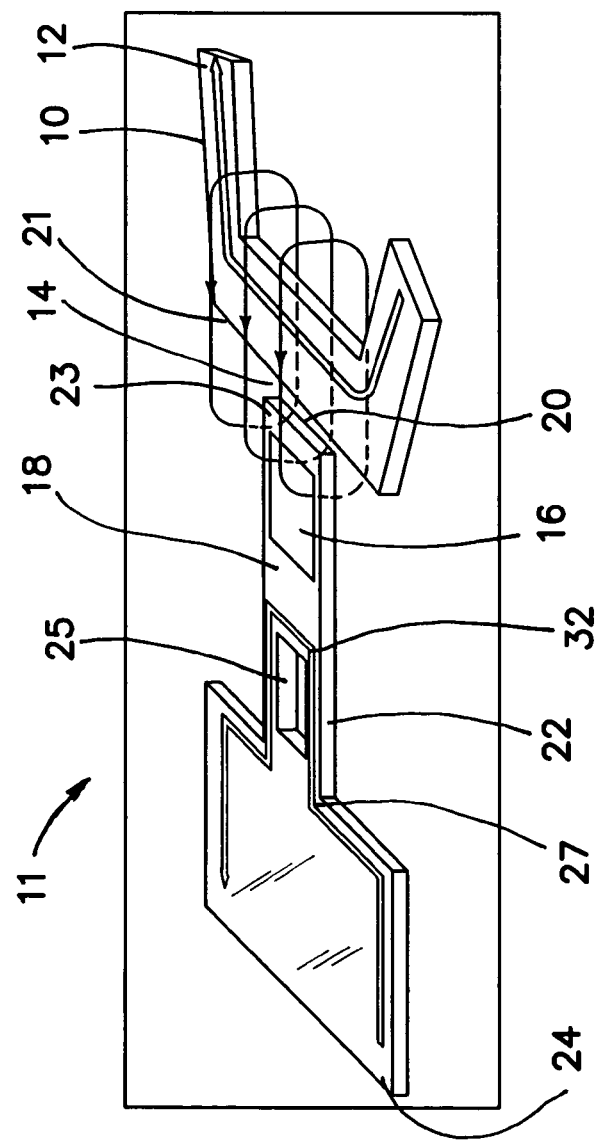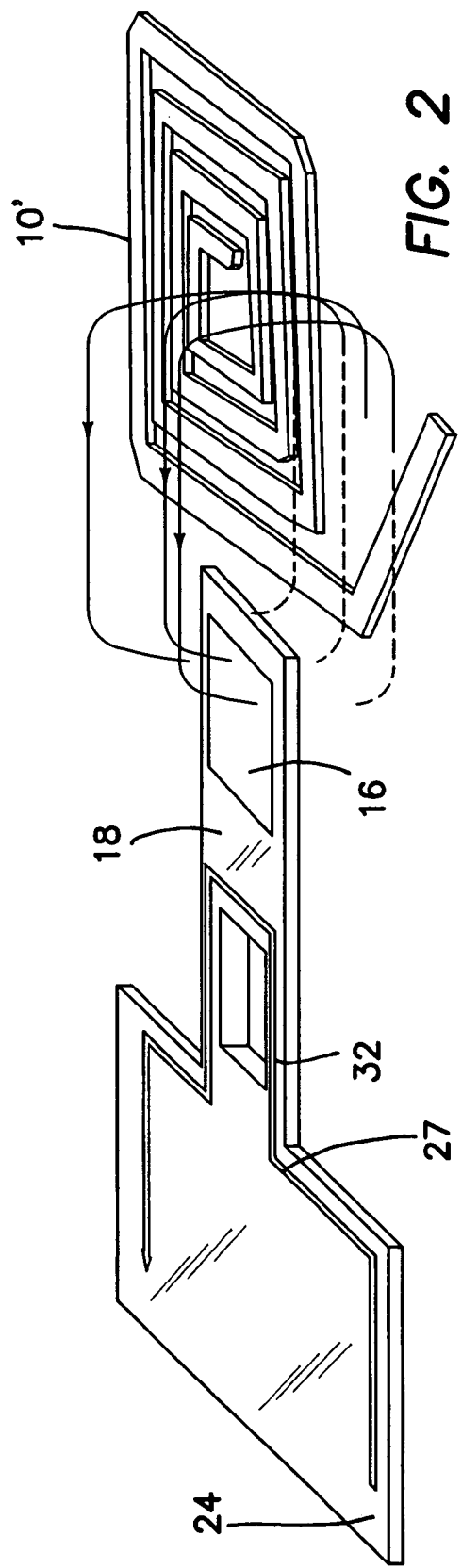

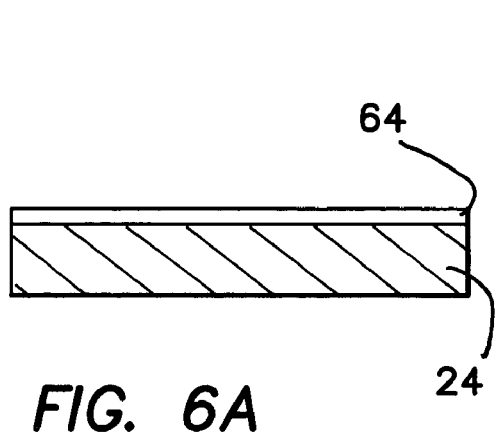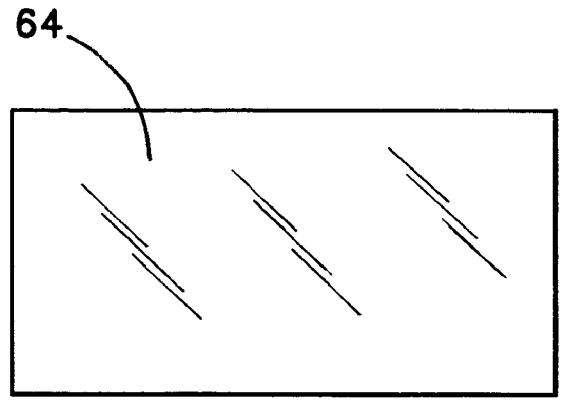
FIG. 6A
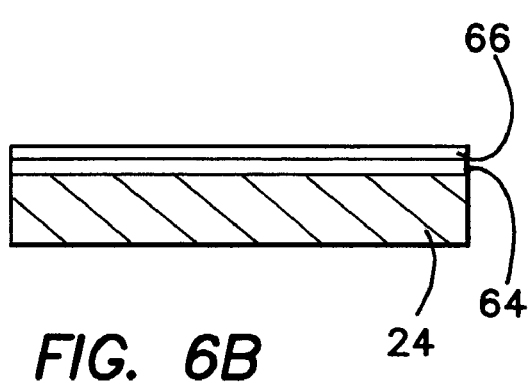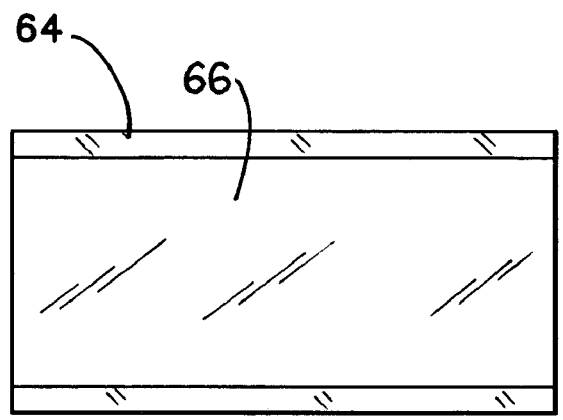
FIG. 6B
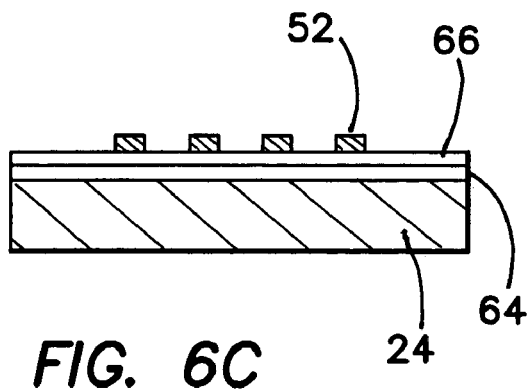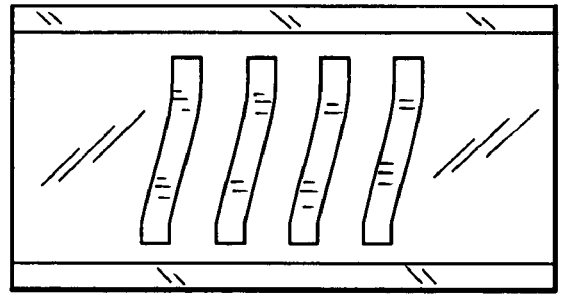
FIG. 6C

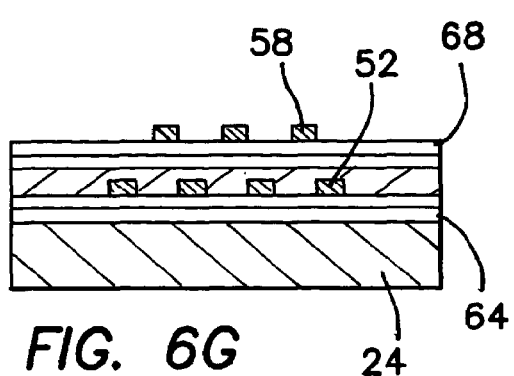
FIG. 6G
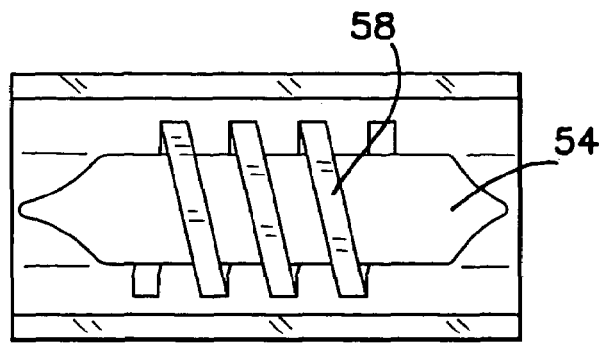
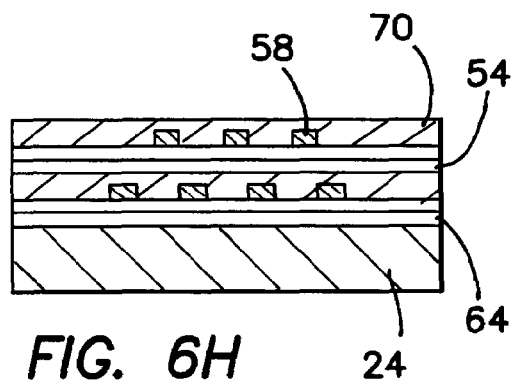
FIG. 6H
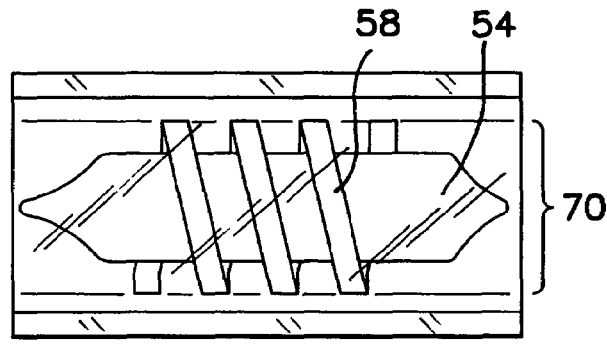
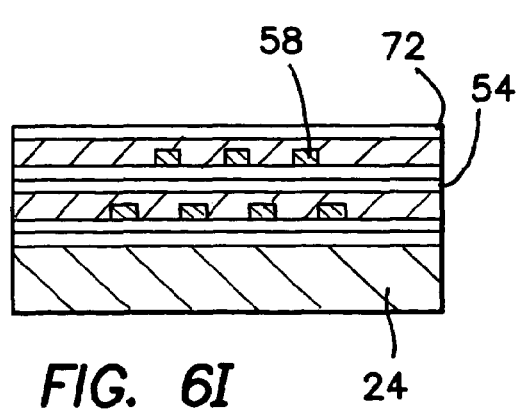
FIG. 6I
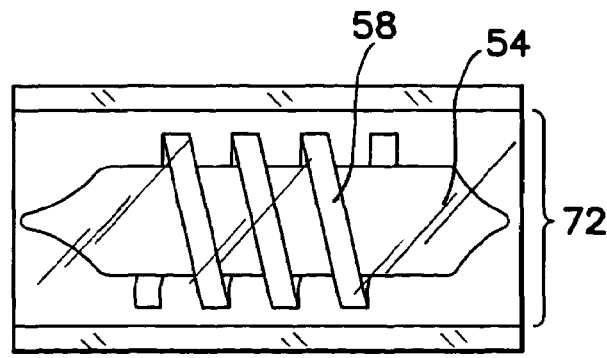

ON-CHIP MAGNETIC FORCE ACTUATION OF MICROCANTILEVERS BY COPLANAR COILS

RELATED APPLICATIONS

The present application is related to U.S. Provisional Patent Application Ser. No. 60/461,257, filed on Apr. 8, 2003, which is incorporated herein by reference and to which priority is claimed pursuant to 35 USC 119.

The U.S. Government has certain rights in this invention pursuant to Grant No. F49620-02-1-0085 awarded by the Air Force.

BACKGROUND OF THE INVENTION

1. Field of the Invention

The invention relates to on-chip coils for magnetic actuation of nanoelectromechanical devices, and in particular to piezoresistive microcantilevers as part of actuators with biofunctionized cantilever arrays in hybrid semiconductor-microfluidics devices for the analysis and detection of biological entities.

2. Description of the Prior Art

Micro- or nanomachined cantilevered beams which have been biofunctionalized are well known as is their proposed use to detect the presence of bioanalytes by means of changes in the mass of the cantilever and hence its resonant frequency or dynamic performance. However, such bioanalytes are typically carried in a solution which serves to dampen the motion of the cantilever. Thus, one of the challenges has been to obtain a high enough signal from the thermal oscillations of the cantilever or to otherwise effectively drive the cantilever so that its dynamic performance could be usefully utilized to generate an output signal with an acceptable signal-to-noise ratio.

BRIEF SUMMARY OF THE INVENTION

In the illustrated embodiment the invention is a micromachined oscillating cantilever system comprising a micromachined target cantilever, a magnetic element disposed on the target cantilever, and a micromachined on-chip coil disposed adjacent to the magnetic element and separated therefrom by a predetermined gap. The on-chip coil is provided with a current which magnetically couples with the magnetic element to oscillate the target cantilever. A transducer is coupled to the target cantilever to generate a signal in response to oscillation of the target cantilever.

The micromachined planar coil comprises many turns or a partial turn of micromachined conductive wires, which in the illustrated embodiment is a quarter turn of circular loop.

In the preferred embodiment the micromachined target cantilever, magnetic element and micromachined coil are substantially coplanar.

In one application of the invention the cantilever system further comprises a microfluidic device having a microfluidic channel with a planar aspect. The micromachined target cantilever, magnetic element and micromachined coil are disposed in the planar aspect of the microfluidic channel.

The cantilever system further comprises a dummy micromachined target cantilever disposed in a parallel relationship with the target cantilever and symmetrically disposed with the target cantilever relative to the micromachined planar coil.

The cantilever system further comprises a target spring coupled to the target cantilever about which target spring the target cantilever oscillates and where the transducer comprises a piezoresistive target resistor coupled to the target spring. The piezoresistive target resistor is preferably formed into the target spring. In the illustrated embodiment the target spring comprises a pair of parallel arms acting as a two-dimensional hinge defining an axis about which the target cantilever oscillates. In this embodiment the piezoresistive target resistor is formed into each arm of the target spring.

The cantilever system further comprises a dummy spring coupled to the dummy cantilever about which dummy spring the dummy cantilever oscillates. The transducer comprises a piezoresistive dummy resistor coupled to the dummy spring. Similarly, the piezoresistive dummy resistor is formed into the dummy spring.

The target piezoresistor and dummy piezoresistor are combined in a circuit to form a balancing bridge. The target cantilever and dummy cantilever being fabricated as substantially duplicated cantilevers.

In the illustrated embodiment the cantilever system further comprises a preamplifier fabricated on chip with the target cantilever and dummy cantilever.

The on-chip coil is either micromachined solenoid coil or planar coil. The solenoid coil is fabricated through multi-layer lithography processes. The solenoid has multiple turns of conducting wires and contains a magnetic core to enhance the magnetic field intensity. The end of the core facing the cantilever is sharpened to concentrate magnetic fluxes and provide a high magnetic gradient at the cantilever magnet. The planar coil is a flat, thick micromachined wire of having a resistance of 1 ohm or less.

The invention can be implemented as a plurality of target cantilevers, magnetic elements, on-chip coils and transducers combined to provide cantilever systems in an array. At least some of the plurality of target cantilevers are selectively biofunctionalized.

The invention has includes within its scope the method of operating and manufacturing the above micromachined oscillating cantilever system.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1 is a perspective diagram of a single magnetic nanomachined cantilever disposed in a field produced by a current line.

FIG. 2 is a perspective diagram of a single magnetic nanomachined cantilever disposed in a field produced by a multi-turn planar coil

FIGS. 6a–6i is a process flow for micromachining solenoid coil.

FIG. 9b is a graph of the piezoresponse in μV of a conventional thermally driven cantilever as compared to the magnetically driven cantilever of FIGS. 1–4a.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 11:
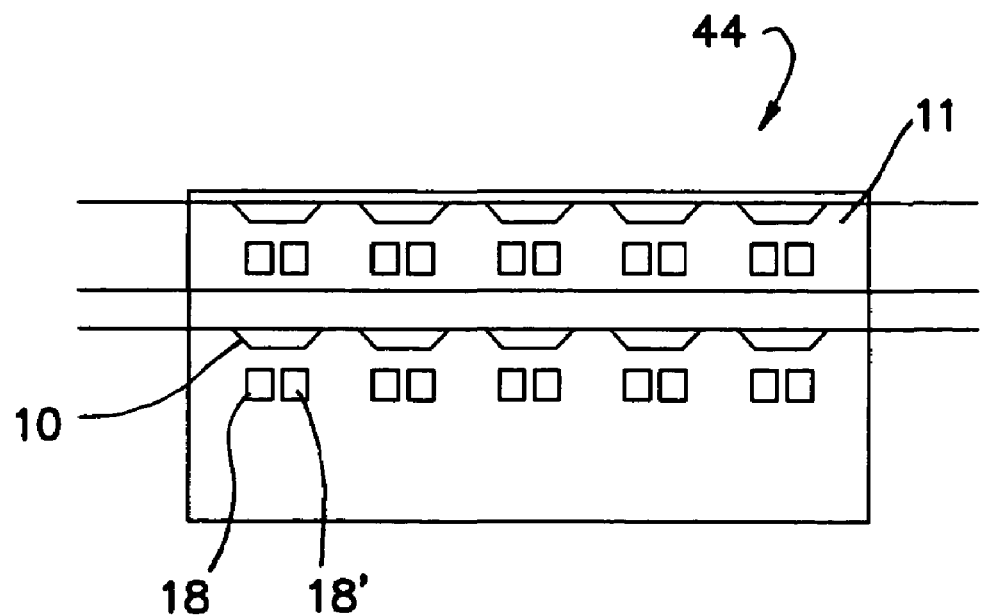
FIG. 11 is a diagrammatic top plan view of array of dual cantilever system of the invention.

An on-chip magnetic coil is provided in a micromachined device for magnetic actuation of a nanoelectromechanical microcantilever. Three kinds of magnetic coils are designed for this purpose. The simplest one involves a straight conductor line carrying high current that generates a large enough magnetic field in its close proximity to a permalloy thin film patch disposed on the distal end of the piezoresistive microcantilever to effectively interacts with the magnetic thin film deposited on the microcantilever. A more complicated multiturn two dimensional planar coil can also be used to enhance the generated magnetic field. A novel three dimensional micro-solenoid can provide the strongest electromagnetical actuation. This microcoil can be microfabricated and integrated to the side of the cantilever and supply a large magnetic field and field gradient. The device comprises an effective actuators which can be integrated with biofunctionized cantilever arrays in hybrid semiconductor-microfluidics devices for the analysis and detection of biological analytes. FIG. 11 is a top plan diagrammatic view of an array of a plurality of cantilever systems 11, each incorporating a microcoil 10, and dual cantilevers 18 and 18'. The current wires 10 may be in common circuit with each other, while each set of dual cantilevers 18 and 18' forming a bridge circuit with its on-chip transducer 28 can be addressed using conventional digital addressing protocols. Each cantilever or each subset of cantilevers may be provided with a different type of biofunctionalized selective chemical attractor disposed on the target cantilever 18 so that a broad range of bioanalytes or other chemical factors may be detected and quantified.

Actuator design

Figure 10:
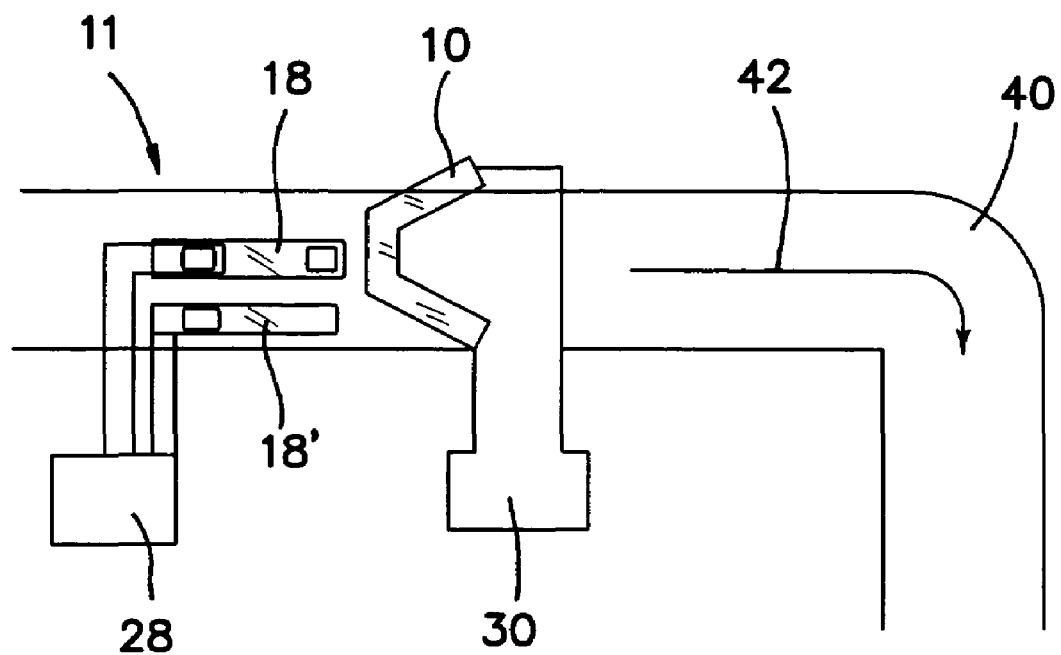
FIG. 10 is a diagrammatic top plan view of a dual cantilever system of the invention disposed in a fluidic channel of a microfluidic device.

Planar coils or current lines or three dimensional microsolenoid 10 are illustrated in the invention for an integrated nano- or micromachined actuation and sensing system 11. The use of a planar geometry allows for the use of optical microscopy without placing a length restriction on the sample, and allows for easier sample preparation. This choice of coil design also enables a higher gradient strength necessary for cantilever actuation as this kind of coil may be placed as close as necessary to the cantilever 18. Disclosed below are designs for a single field generating current line or multi-turn two dimensional planar coil or three dimensional micro-solenoid 10 which permits easy access to a microscope and is especially adapted to integration into microfluidics channels. FIG. 10 is a simplified top plan view of cantilever system 11 disposed in a microfluidic channel 40 in a flow 42 of analyte. Channel 40 may have one or more flat walls in which a plurality of cantilever systems 11 may be deployed and fabricated in an integrated fashion with their corresponding transducing circuits 28 and drive circuits 30.

Coil Design 1-Field Generating Current Line (a Quarter Turn Coil)

FIG. 1 is a perspective diagram which illustrates the concept of a magnetic field generated by a planar current line 10. A large drive current 12, symbolically shown in FIG. 1 as an arrow on current line 10, is coupled to a thick gold wire which comprises current line 10 to generate a local magnetic field, which current line 10 in the illustrated embodiment is approximately 600 nm thick, and 10 μm wide. Field 14 is symbolically depicted in FIG. 1 by field line 14. To efficiently provide a local drive to a cantilever 18, a 300 nm thick permalloy thin film 16 of size 3 μm by 4 μm is deposited at the end of the cantilever 18. The gap 20 between the near edge 21 of the current line 10 and permalloy film 16 is about 3 μm. The deflection for the cantilever 18 is modeled using the force balance between the force experienced by permalloy film 16 and the resilient restoring force of the cantilever springs 22. Springs 22 are formed by removing a portion 25 from cantilever 18 proximal from film 16. Cantilever 18 is fabricated from a piezoresistive material and deflections of cantilever 18 are measured using a sense current line 27 which is disposed over springs 22.

The force load to the cantilever 18 produced by the interaction between coil generated field 14, B, and the magnetic moment of m in the permalloy film 16, $$F_{NiFe,z} = |\vec{m}_{NiFe} \cdot grad\vec{B}_{coil}| = \int m_{NiFe,x} \frac{\partial B}{\partial x} dx = M_s W d(B_{x=r_0} - B_{x=r_0+L}) \quad (1)$$

where $M_s$ is the saturation magnetization of film 16, L, W, d are the length, width and thickness of the permalloy film 16, $r_0$ is the distance from the center of the write or current line 10 to the edge of the permalloy film 16. Here we also assume that the permalloy film 16 is fully magnetized in-plane prior to the application of the drive current 12 by conventional means. The magnetic field generated by current line 10 can be approximated by, $$B = \mu_0 I / 2\pi r \quad (2)$$

By plugging equation 2 into equation 1, the net force along deflection direction can be calculated, $$F_{NiFe,z} = M_s V_{NiFe} \mu_0 / 2\pi r_0 (r_0 + L) \quad (3)$$

Here $V_{NiFe}$ is the volume of the permalloy film 16, $V^{NiFe} = 3.6 \times 10^{-18}$ m$^3$. The saturation magnetization of permalloy film 16 is $M_s = 8.6 \times 10^5$ A/m. Therefore, the magnetic force at 200 mA drive current is −1.4 nN. This amount of force is more than 200 times larger than the thermal mechanical actuation force in conventionally thermal driven cantilevers. Counting for the fact that the magnetic moment might not be fully aligned along the x direction, the force could be deteriorated by a numerical factor. It is, however, sufficient for active actuation and analysis of biofunctionalized cantilevers, i.e. cantilevers which have been provided with a sensitized surface to selectively adhere to an analyte contacting the surface and consequently change the cantilever's mass and resonance frequency as a result.

Coil Design 2—Multi-Turn Planar Coil

Instead of using a simple straight line 10 to generate magnetic field, a more complicated two dimensional planar coil 10' can be employed to provide higher magnetic field. FIG. 2 is a perspective view showing the configuration of the planar coil 10'. The coil 10' may be formed as a rectangular or circular spiral and can be batch-fabricated along with the cantilevers 18.

Coil Design 3—Three Dimensional Micro Solenoid

Figure 3:
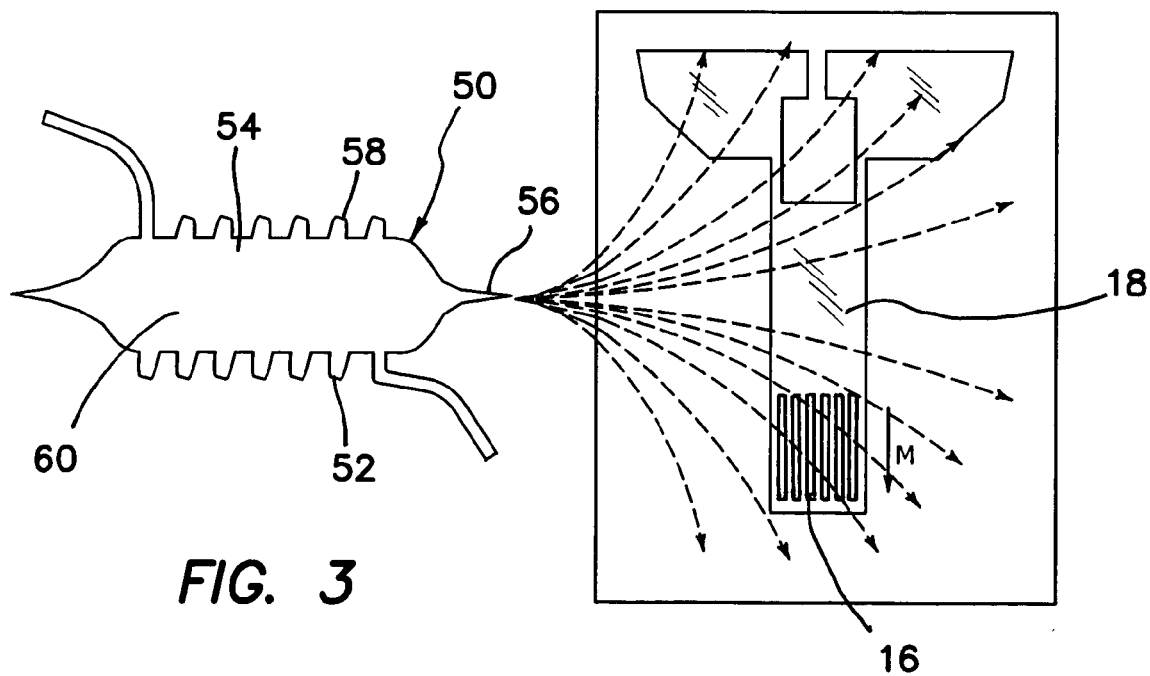
FIG. 3 is a perspective diagram of a single magnetic nanomachined cantilever disposed in a field produced by a micromachined solenoid with a sharpened magnetic core.
Figure 6D:
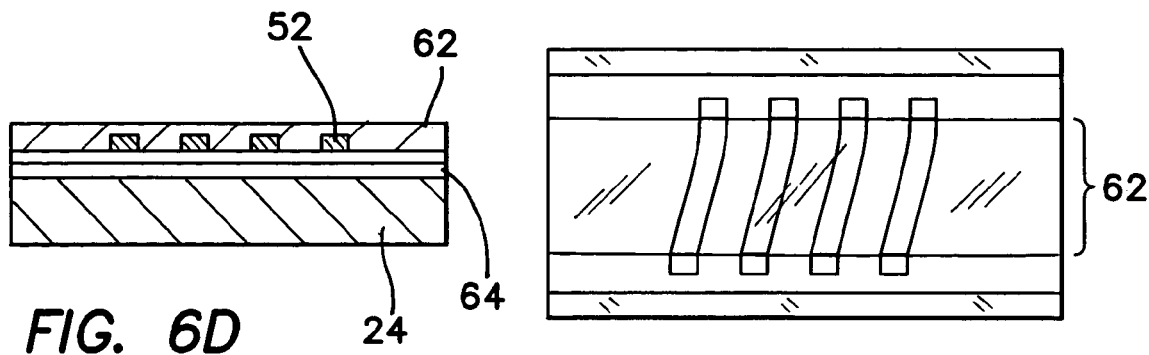
Figure 6E:
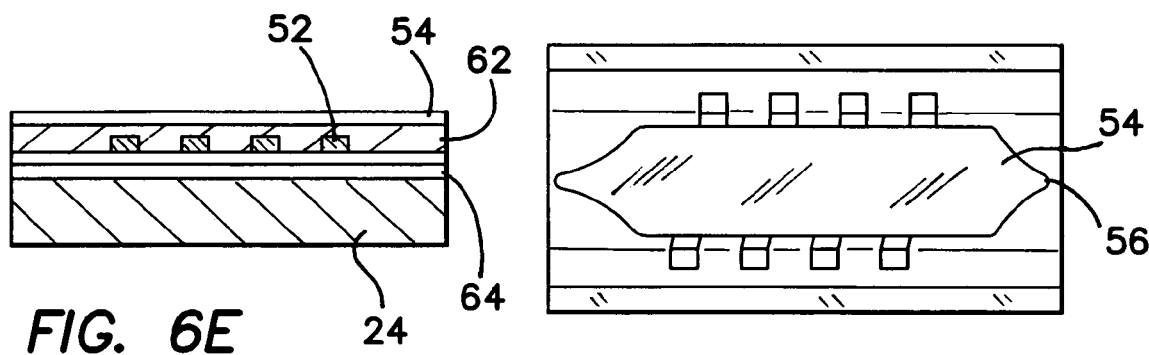
Figure 6F:
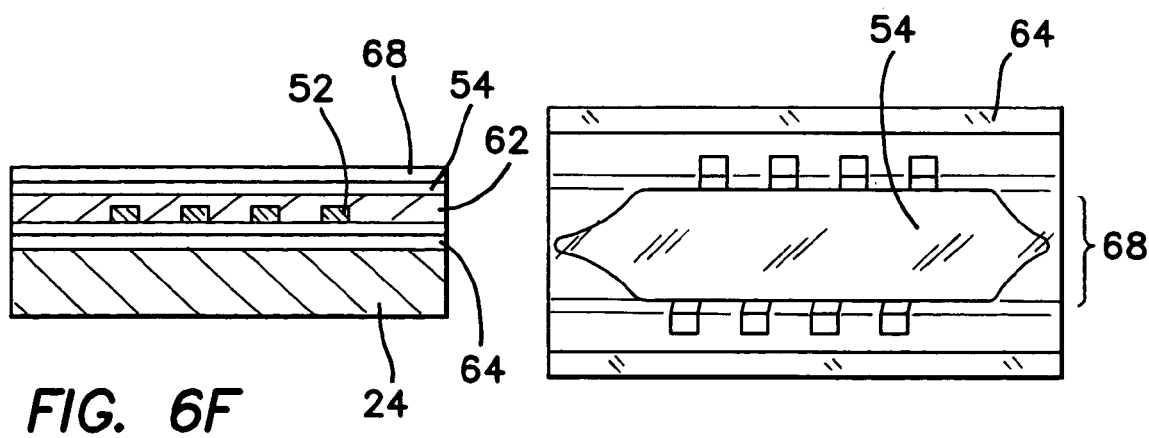

FIG. 3 shows a top plan view of the micro-solenoid 50 and the cantilever 18. FIGS. 6a–6i illustrate the fabrication process of three dimensional solenoid 50 with a diagrammatic side cross-sectional view shown on the left and its corresponding top plan view on the right in a pair wise fashion. FIG. 6a shows chip 24 being coated with a Cu or other conductive coating 64, which in the illustrated embodiment is 30 nm thick. Thereafter a 1 µm insulator layer 66, such as SiN, is disposed on conductive coating 64 as depicted in FIG. 6b. The metal wires fabrication is decomposed into three parts: The bottom conductors 52, the top conductors 58 and the interconnection vias 60. They are all formed by photolithography followed by electroplating. Bottom coils 52 are selectively electroplated on insulator layer 66 as shown in FIG. 6c. An insulating layer 62 is photolithographically deposited on bottom coils 52 as shown in FIG. 6d, such as deposition of a 1 µm layer of photoresist which is then cured, or plasma enhanced chemical vapor deposition (PECVD) of a layer of SiO$_2$. The lateral ends of bottom coils 52 remain selectively exposed and are not covered by the final configuration of layer 62, leaving the lateral ends available for later electrical connection with vias 60 in FIG. 6g. The magnetic core 54 is first phtolithographically defined and then electroplated in Ni as depicted in FIG. 6e. The tip 56 is patterned by photolithography or by electron beam lithography as best shown in the right portion at the step of FIG. 6e. A second insulating layer 68 is disposed on core 54 at the step of FIG. 6f, again leaving the lateral ends of bottom coil 52 free for later electrical connection. Top coils 58 are then selectively electroplated in Cu or Au onto layer 68 and vertical vias 60 connecting top coils 58 to bottom coils 52 formed across each of the sides of the insulated core sandwich of layers 62, 54, 68 thereby completing the spiral circuit of coils around magnetic core 54 as shown in FIG. 6g. Thereafter, a cap layer 70 of photoresist or SiO$_2$ is disposed over top coils 58 and layer 68 as seen in FIG. 6h. Further encapsulatization with a metal/SiN heterolayer 72 is then disposed over solenoid 50 as shown in FIG. 6i to provide for electrical shielding and passivation of solenoid 50.

The force generated by the interaction between the magnetic tip 56 and magnetic moment ($M_x$, $M_y$, $M_z$) on the end of the cantilever 18 can be expressed as, $$F_z = M_x \frac{\partial B_x}{\partial z} + M_y \frac{\partial B_y}{\partial z}$$

Assume the end of the tip 56 generates a field like a dipole moment, the magnetic field can be written as, $$B_x = \frac{\mu_0 M}{4\pi} \left[ \frac{3x^2 - r^2}{r^3} \right], \quad B_y = \frac{\mu_0 M}{4\pi} \left[ \frac{3yz}{r^5} \right]$$

Thus the magnetic force can be calculated.

Even though difficult to manufacture, solenoid actuator 50 of FIG. 3 has several advantages over the previous two designs. Only bottom conductor lines 52 occupy areas on the surface of the chip 24, so that both the size and stray capacitance can be small; a high concentration of flux can be achieved by merely increasing the number of turns with a relatively small increase in area occupation. A magnetic core 54 made of high susceptibility soft magnetic material can be implemented to enhance the magnetic field in the coil 50. The magnetic coil 50 can be extended to the proximity of the cantilever magnet 16 without losing magnetic flux inside the core 54, while the solenoid 50 can be placed further away from the cantilever 18. Most importantly, the end of the magnetic core 54 can be made into a flux concentrator shape or a tip 56 to focus the magnetic field. At the end of this tip 56, the magnetic field gradient is enhanced by several magnitudes.

Nanomagnet Design

To maximize the magnetic force, the magnetic pad 16 on the cantilever 18 should be optimally designed. One approach is to make the magnet 16 in a single domain state so that magnetization is always saturated and provided the largest magnetic response.

Figure 4A:
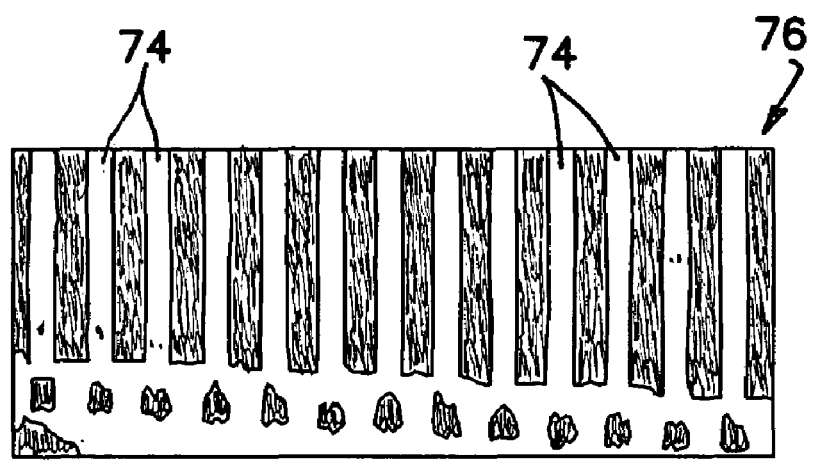
FIG. 4a is a scanning electron micrograph of a nanomagnet array that serves as magnetic actuator component on the cantilever.
Figure 4B:
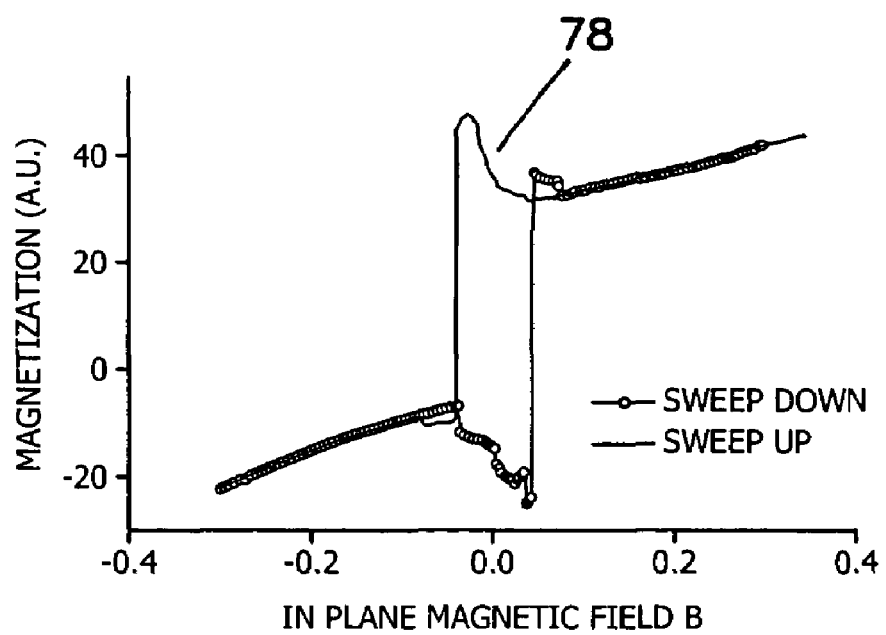
FIG. 4b is a graph of the magnetization of the nanomagnet array of FIG. 4a as a function of the applied planar magnetic field, B.

For a thin film magnet, this can be achieved by an array 76 of single magnets 74 as shown in the microphotograph of FIG. 4a. If the magnets 74 are patterned with a length/width aspect ratio greater than 5 and width of less than 1 µm, due to the shape anisotropy of the magnetic material, the nanomagnet 74 will stay in a single domain state after initial magnetic treatment. Many of such nanomagnets 74 can be put in parallel to yield a higher total magnetization while maintaining single domain state. FIG. 4a shows a SEM image of such a nanomagnet array 76. An optimum geometry is 10 µm length×0.5 µm width×75 nm thick. FIG. 4b is a graph of the experimentally measured magnetization of array 76 as a function of applied in-plane magnetic field, B, which shows the magnetic transition curve of array 76 of magnets 74. Simultaneous switching of all magnets 74 is confirmed by the observed transition region 78.

Figure 5F:
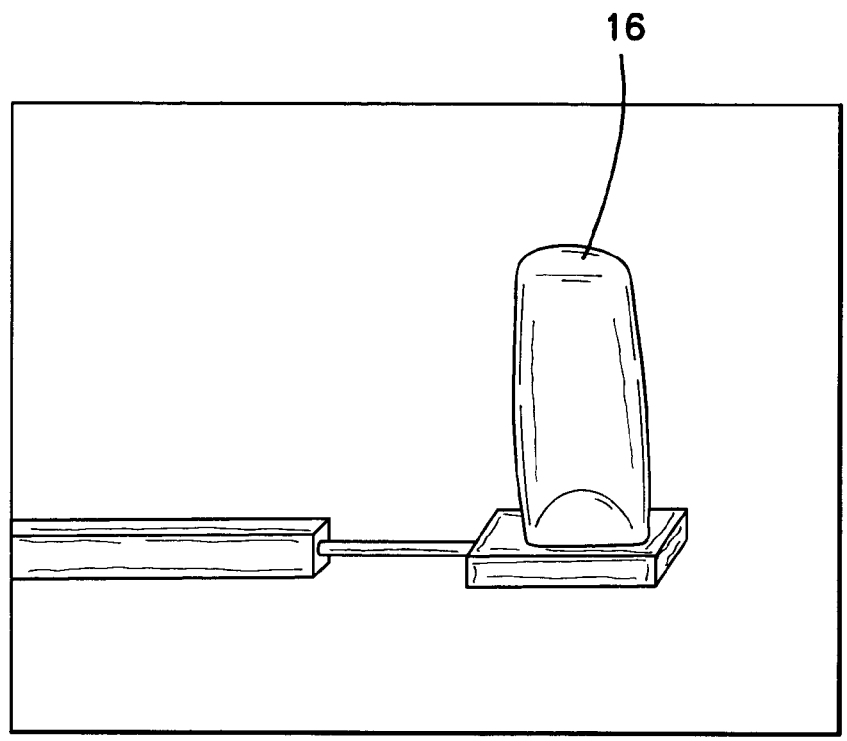
FIG. 5f is a scanning electron micrograph of the electroplated columnar nanomagnet made by the method of FIGS. 5a–5e.
Figure 5A:
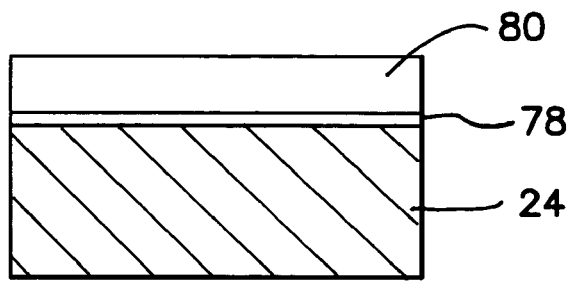
FIGS. 5a–5e are diagrams which depict the process by which an electroplated columnar nanomagnet is fabricated on the cantilever.
Figure 5B:
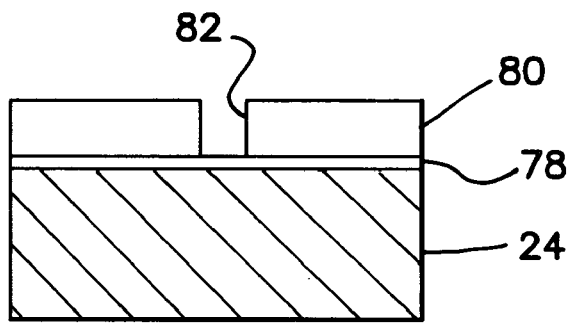
Figure 5C:
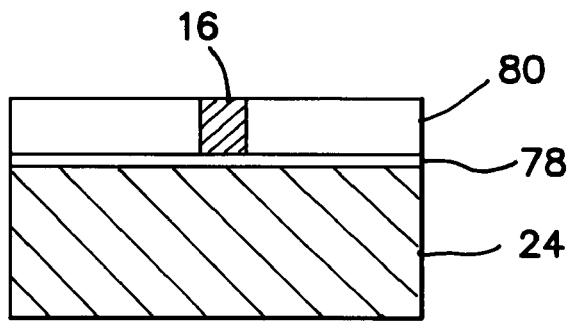
Figure 5D:
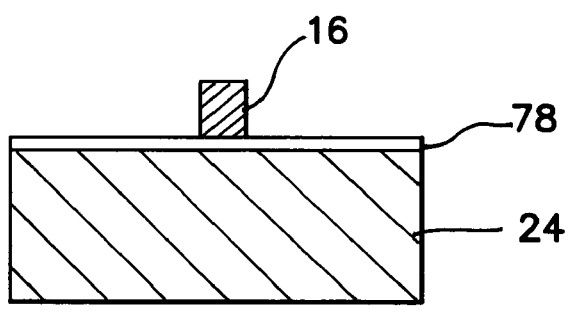
Figure 5E:
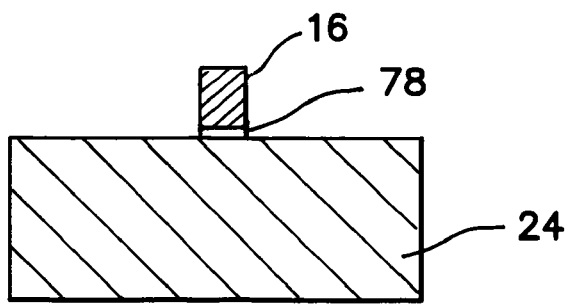

On the other hand, a large force can be simply obtained by increasing the volume of the magnet 16 on the cantilever 18 while maintaining some aspect ratio. FIG. 5f is a microphotograph which shows an electroplated magnet 16 with aspect ratio approximately 3 and diameter of approximately 600 nm. A diameter of 200 nm with aspect ratio of 5 has also been realized. Magnet 16 is deposited at the end of the cantilever 18 by electroplating Permalloy into an electron beam defined polymethylmethacrylate (PMMA) mold. The fabrication process is diagrammatically depicted in FIGS. 5a–5e. In FIG. 5a, an aluminum seed layer 78 is first deposited by thermal or electron beam evaporation on chip or wafer 24. A very thick PMMA layer 80 (11%, 495K) is then spin coated on the seed layer 78 as shown in FIG. 5a. After electron beam exposure and after development of a high aspect ratio hole 82 is formed in PMMA layer 80 as shown in FIG. 5b. The magnetic material is placed in a permalloy plating solution and a column magnet 16 of NiFe is plated through the PMMA hole 82 as shown in FIG. 5c. PMMA layer 80 is removed in acetone as shown in FIG. 5d. The seed layer 78 is removed by wet or dry etching as shown in FIG. 5e.

Transducer Design

Sensing of the cantilever deflection is achieved by piezoresistive p-doped surface silicon layers 24 defined onto springs 22. The cantilever thickness is t=110 nm, of which the top 30 nm forms the piezoresistive conducting layer (with a boron doping density of $4\times10^{19}/cm^3$). The transducer and its leads 27 are patterned on this top layer 24. To concentrate the strain to this piezoresistive area, the material between the conducting leads 27 are removed as shown in FIG. 1. To minimize the electrostatic coupling between transduction circuit 28 and drive circuit 30 schematically shown in FIG. 8, it is essential to electrically separate the transducer region 32 from the actuator provided by permalloy film 16. The output of the transducer is fed into a high impedance low noise preamplifier 34.

Device Layout and Fabrication

Fabrication starts from a SIMOX wafer (Separation by Implantation of Oxygen) with 80 nm intrinsic or i-Si layer and 400 nm $SiO_2$ layer. Boron- or -doped silicon is then grown on the i-Si layer and thinned down to 30 nm by etching. A square membrane of 110 nm thick p+Si/i-Si structure layer is fabricated through a DRIE etching (Deep Reactive Ion Etching) method. After the $SiO_2$ is removed, metallic contacts are deposited by photolithography and lifted off.

The current line 10 and cantilevers 18 are defined by electron beam lithography (EBL). The EBL pattern design is shown in the top plan view of FIG. 7. In order to achieve a higher current level, the current line 10 is made of very wide and thick pure gold (10 μm×600 μm). The resistance of the resulted conductor wire 10 is designed to be less than 1 Ohm.

Figure 8:
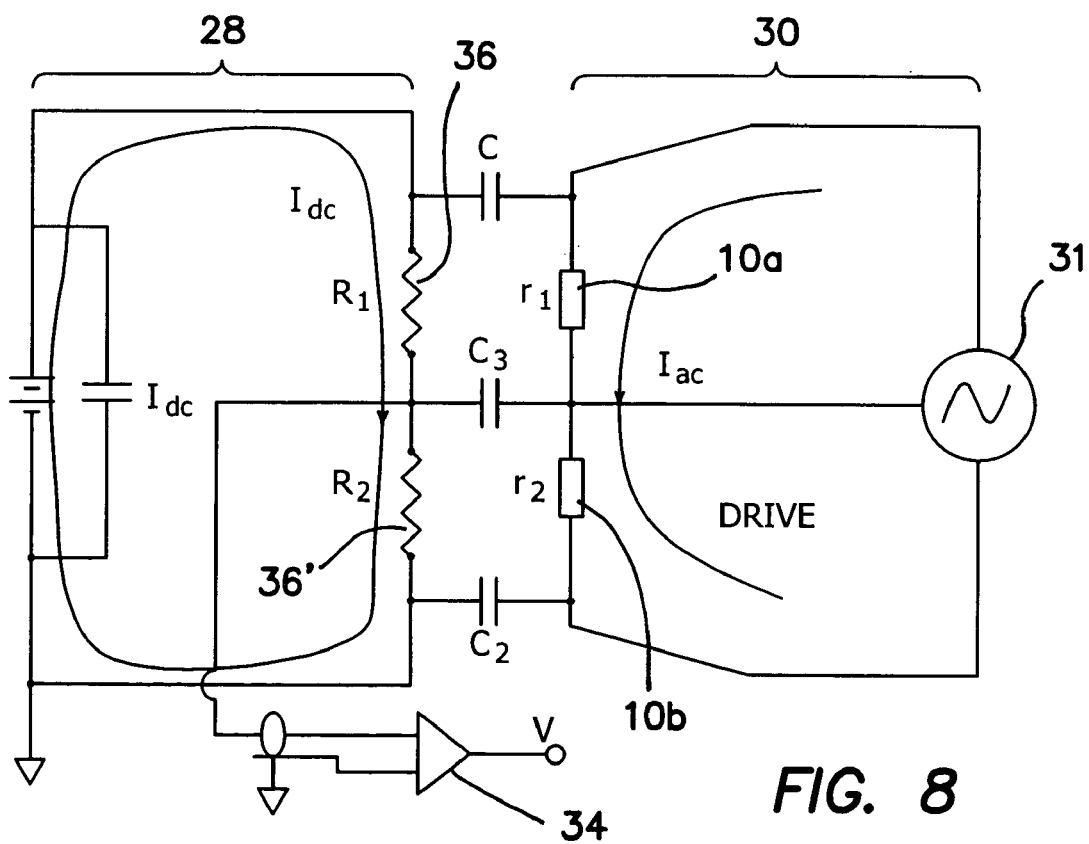
FIG. 8 is an equivalent circuit for cantilever actuation and signal transduction for the cantilever system of FIG. 7.

To extract the piezoresistive signal, a constant DC current of around 20 μA is flown through the arms or springs 22 of the cantilever 18. Usually a piezoresistor has a high resistance that could generate a large DC voltage background as well as the expected oscillating AC signal. An on-chip balance resistor 36 as shown in FIG. 8 is necessary to null the DC offset. Here we use an identical cantilever 18' as the balance resistor 36'. The AC signal is pulled out at the center point of these two resistors 36 and 36' and coupled to an on-chip preamplifier 34 as shown in FIG. 8. This design also has the benefit of canceling drifts due to temperature change and environmental changes in liquids in which cantilevers 18 and 18' might be immersed.

Figure 7:
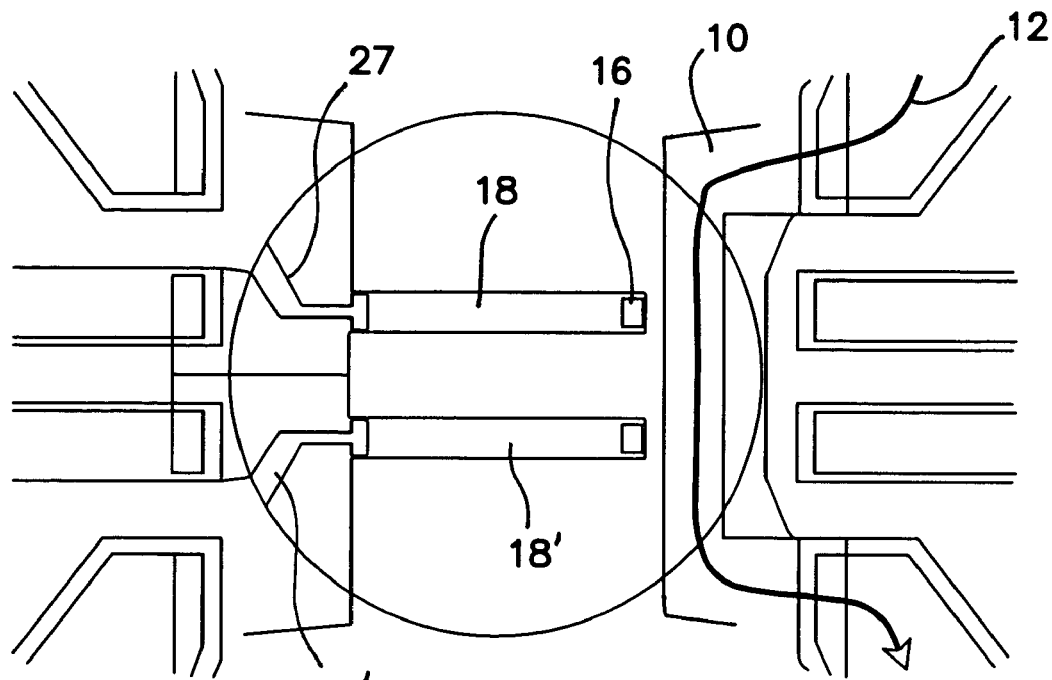
FIG. 7 is a top plan view of a pattern for a magnetic nanomachined cantilever and current line of the invention utilizing a dual dummy cantilever.

Most importantly, this additional cantilever 18' could be used to annul the crosstalk from the drive circuit 30. Unlike optical interferometers, piezoresistive transducers are extremely vulnerable to parasitic coupling from drive electrodes. This parasitic signal could dominate mechanical response and saturate the detection electronics. Here, by arranging the sensor resistor 36 and balance resistor 36' in a very symmetric way, the direct AC coupling could be completely compensated in an optimum situation. The equivalent electrical circuit is sketched in FIG. 8, in which $R_1$, $R_2$ are cantilever resistances 36, 36' varying from 20 kΩ to 200 kΩ, $r_1$ and $r_2$ (<0.5Ω) are resistances 10a and 10b of the top and bottom part of the current line 10 as shown in FIG. 7 which is driven by driving current source 31. $C_1$, $C_2$ and $C_3$ are effective parasitic capacitors corresponding to coupling between line 10 and cantilevers 18 and 18'. A detailed analysis of this circuit gives an output voltage at preamplifier 34 as:

$$V = \frac{I_{dc}\delta R}{1 + \frac{R_1}{\left(R_2 // \frac{1}{i\omega C_0}\right)}} +$$

$$I_{ac}\left[\frac{r_1}{1 + \frac{1/i\omega C_1}{1/i\omega C_2 // (1/i\omega C_3 + R_1 // R_2)}} - \frac{r_2}{1 + \frac{1/i\omega C_2}{1/i\omega C_1 // (1/i\omega C_3 + R_1 // R_2)}}\right]$$

where $I_{dc}$ is the dc current component in the transducer circuit 28, $I_{ac}$ is the ac current component in the drive circuit 30 and $\delta R = R_1 - R_2$. The second term, representing direct AC coupling, approaches zero in an optimized situation, where $r_1 = r_2$ and $C_1 = C_2$.

Devices

Figure 9A:
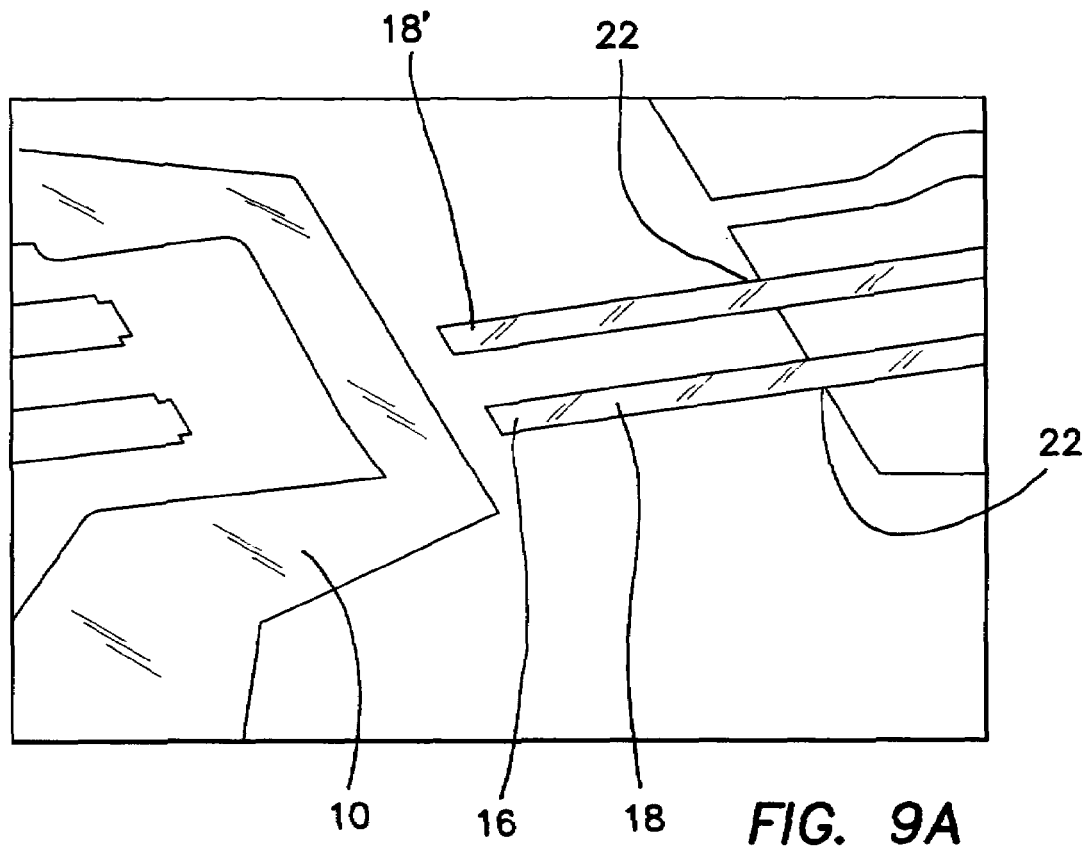
FIG. 9a is a scanning electron microscopic photograph of an actual device made according to FIGS. 2 and 3.
Figure 9B:
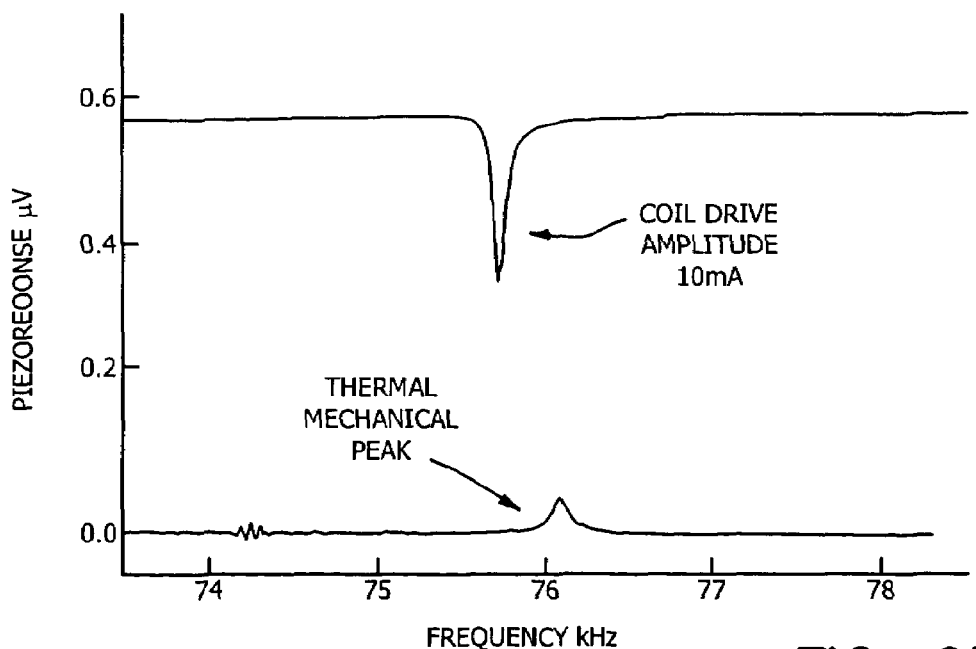

An SEM micrograph of a finished device is shown in FIG. 9a. The conductor 10 is 600 nm thick gold current line. The target cantilever 18, distinctive from the dummy cantilever 18' by having bright permalloy pad 16 on its distal tip, is about 20 μm long. A resonance peak is detected around 76 kHz under 10 mA driving current 12 in the current line 10. In comparison to a thermal mechanically drive amplitude, the force acquired from the magnetic drive is determined to be 16 pN for a 10 mA drive current or 0.32 nN for 200 mA drive current. In the illustrated device, the total resistance in the drive circuit 30 is 200Ω. A maximum current of about 10 mA can readily be supplied. In principle, the total resistance in the drive circuit 30 can be reduced to well below 10Ω, and a current as high as 500 mA can be carried in the current line 10. A strong local force induced by magnetic coupling has thus been clearly demonstrated.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A micromachined oscillating cantilever system comprising:
    a micromachined target cantilever;
    a magnetic element disposed on the target cantilever;
    a micromachined coil disposed adjacent to the magnetic element and separated therefrom by a predetermined gap, the coil being provided with a current which magnetically couples with the magnetic element to oscillate the target cantilever;
    a transducer coupled to the target cantilever to generate a signal in response to oscillation of the target cantilever; and
    a target spring coupled to the target cantilever about which target spring the target cantilever oscillates and where the transducer comprises a piezoresistive target resistor coupled to the target spring.

2. The cantilever system of claim 1 where the micromachined coil comprises at least a partial turn of a planar loop of a micromachined conductive wire.

3. The cantilever system of claim 2 where the partial turn of the planar loop comprises a quarter turn of circular loop.

4. The cantilever system of claim 1 where the micromachined coil comprises a spiral planar loop of a micromachined conductive wire.

5. The cantilever system of claim 1 where the micromachined coil comprises a solenoidal coil of a micromachined conductive wire.

6. The cantilever system of claim 5 where the solenoidal coil further comprises a magnetic core.

7. The cantilever system of claim 6 where the magnetic core has a micromachined, acutely shaped tip to concentrate a magnetic field produced within the core.

8. The cantilever system of claim 1 where the micromachined target cantilever, magnetic element and micromachined coil are substantially coplanar.

9. The cantilever system of claim 1 where the magnetic element comprises an array of nanomagnets.

10. The cantilever system of claim 9 where the array of nanomagnets comprises a plurality of parallel columnar nanomagnets.

11. The cantilever system of claim 1 further comprising a microfluidic device having a microfluidic channel with a planar aspect and where the micromachined target cantilever, magnetic element and micromachined coil are disposed in the planar aspect of the microfluidic channel.

12. The cantilever system of claim 1 further comprising a dummy micromachined target cantilever disposed in a parallel relationship with the target cantilever and symmetrically disposed with the target cantilever relative to the micromachined coil.

13. The cantilever system of claim 1 where the piezoresistive target resistor is formed into the target spring.

14. The cantilever system of claim 1 where the target spring comprises a pair of parallel arms acting as a two-dimensional hinge defining an axis about which the target cantilever oscillates.

15. The cantilever system of claim 14 where the piezoresistive target resistor is formed into each arm of the target spring.

16. The cantilever system of claim 1 where the coil is a flat, thick micromachined wire of having a resistance of 1 ohm or less.

17. The cantilever system of claim 1 further comprising a plurality of target cantilevers, magnetic elements, coils and transducers combined to provide cantilever systems in an array.

18. The cantilever system of claim 17 wherein at least some of the plurality of target cantilevers are selectively biofunctionalized.

19. A micromachined oscillating cantilever system comprising:
    a micromachined target cantilever;
    a magnetic element disposed on the target cantilever;
    a micromachined coil disposed adjacent to the magnetic element and separated therefrom by a predetermined gap, the coil being provided with a current which magnetically couples with the magnetic element to oscillate the target cantilever;
    a transducer coupled to the target cantilever to generate a signal in response to oscillation of the target cantilever;
    a dummy micromachined target cantilever disposed in a parallel relationship with the target cantilever and symmetrically disposed with the target cantilever relative to the micromachined coil; and
    a dummy spring coupled to the dummy cantilever about which dummy spring the dummy cantilever oscillates and where the transducer comprises a piezoresistive dummy resistor coupled to the dummy spring.

20. The cantilever system of claim 19 where the piezoresistive dummy resistor is formed into the dummy spring.

21. The cantilever system of claim 19 where the piezoresistive target resistor and piezoresistive dummy resistor are combined in a circuit to form a balancing bridge, the target cantilever and dummy cantilever being fabricated as substantially duplicate cantilevers.

22. The cantilever system of claim 21 further comprising a preamplifier fabricated on chip with the target cantilever and dummy cantilever.

23. A method of actuating a micromachined oscillating cantilever system comprising:
providing a current in a micromachined coil disposed adjacent to a magnetic element disposed on a target cantilever and separated therefrom by a predetermined gap to generate a magnetic field;
coupling the magnetic field with the magnetic element;
oscillating the target cantilever in response to the coupling of the magnetic field with the magnetic element;
transducing the oscillation of the target cantilever into a signal responsive to oscillation of the target cantilever; and
where a target spring is coupled to the target cantilever about which target spring the target cantilever oscillates and where transducing the oscillation of the target cantilever comprises generating a signal through a piezoresistive target resistor coupled to the target spring.

24. The method of claim 23 where providing a current in a micromachined coil comprises flowing a current through a partial turn of a planar loop of a micromachined conductive wire.

25. The method of claim 24 where flowing a current through a partial turn comprises flowing current through a quarter turn of circular loop.

26. The method of claim 23 where providing a current in a micromachined coil provides a current in a coil which is substantially coplanar with the micromachined target cantilever, and magnetic element.

27. The method of claim 23 where providing a current in a micromachined coil provides a current in a spiral planar loop of a micromachined conductive wire.

28. The method of claim 23 where providing a current in a micromachined coil provides a current in a solenoidal coil of a micromachined conductive wire.

29. The method of claim 28 where providing a current in a solenoidal coil further comprises generating a magnetic field in a magnetic core within the solenoidal coil.

30. The method of claim 29 where generating a magnetic field in a magnetic core comprises concentrating the magnetic field through a micromachined, acutely shaped tip and coupling the concentrated magnetic field to the magnetic element.

31. The method of claim 23 where coupling the magnetic field with the magnetic element comprises coupling the magnetic field with an array of nanomagnets.

32. The method of claim 31 where coupling the magnetic field with an array of nanomagnets comprises coupling the magnetic field with a plurality of parallel columnar nanomagnets.

33. The method of claim 23 further comprising providing a microfluidic device having a microfluidic channel with a planar aspect and disposing the micromachined target cantilever, magnetic element and micromachined coil in the planar aspect of the microfluidic channel.

34. The method of claim 23 further comprising:
providing the current in the micromachined coil disposed adjacent to a dummy cantilever and separated therefrom by a predetermined gap;
oscillating the dummy cantilever in response to coupling with the current; and
transducing the oscillation of the dummy cantilever into a signal responsive to oscillation of the dummy cantilever.

35. The method of claim 23 where generating a signal through a piezoresistive target resistor coupled to the target spring comprises generating a signal through a piezoresistive target resistor formed into the target spring.

36. The method of claim 35 where generating a signal through a piezoresistive target resistor comprises generating a signal through a piezoresistive target resistor formed in a pair of parallel arms acting as a two-dimensional hinge defining an axis about which the target cantilever oscillates.

37. The method of claim 23 where providing the current in the micromachined coil provides the current in a flat, thick micromachined wire of having a resistance of 1 ohm or less.

38. The method of claim 23 further comprising:
providing a current in a plurality of micromachined coils disposed adjacent to a plurality of corresponding magnetic elements disposed on the target cantilevers and separated therefrom by a predetermined gap;
oscillating the plurality of target cantilevers in response to their magnetic couplings; and
transducing the oscillation of the plurality of the target cantilevers into a plurality of corresponding signals responsive to oscillation of the respective target cantilevers combined to provide cantilever systems in an array.

39. The method of claim 38 wherein transducing the oscillation of the plurality of the target cantilevers transduces at least some of the plurality of target cantilevers which are selectively biofunctionalized.

40. A method of actuating a micromachined oscillating cantilever system comprising:
providing a current in a micromachined coil disposed adjacent to a magnetic element disposed on a target cantilever and separated therefrom by a predetermined gap to generate a magnetic field;
coupling the magnetic field with the magnetic element;
oscillating the target cantilever in response to the coupling of the magnetic field with the magnetic element;
transducing the oscillation of the target cantilever into a signal responsive to oscillation of the target cantilever;
providing the current in the micromachined coil disposed adjacent to a dummy cantilever and separated therefrom by a predetermined gap;
oscillating the dummy cantilever in response to coupling with the current;
transducing the oscillation of the dummy cantilever into a signal responsive to oscillation of the dummy cantilever; and
where oscillating the dummy cantilever comprises oscillating the dummy cantilever about a dummy spring and where transducing the oscillation of the dummy cantilever comprises generating a signal through a piezoresistive dummy resistor coupled to the dummy spring.

41. The method of claim 40 where generating a signal through a piezoresistive dummy resistor comprises generating a signal through a piezoresistive dummy resistor formed into the dummy spring.

42. The method of claim 40 where transducing the oscillation of the target and dummy cantilevers comprises combining the piezoresistive target resistor and piezoresistive dummy resistor in a circuit to form a balancing bridge, the target cantilever and dummy cantilever being fabricated as substantially duplicate cantilevers.

43. The method of claim 42 further comprising amplifying an output from the bridge with a preamplifier fabricated on chip with the target cantilever and dummy cantilever.

* * * * *